United States Patent
Mendrok-Edinger

(10) Patent No.: US 11,547,646 B2
(45) Date of Patent: Jan. 10, 2023

(54) TOPICAL COMPOSITION

(71) Applicant: DSM IP ASSETS B.V., Heerlen (NL)

(72) Inventor: Christine Mendrok-Edinger, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 52 days.

(21) Appl. No.: 17/056,256

(22) PCT Filed: May 13, 2019

(86) PCT No.: PCT/EP2019/062206
§ 371 (c)(1),
(2) Date: Nov. 17, 2020

(87) PCT Pub. No.: WO2019/219606
PCT Pub. Date: Nov. 21, 2019

(65) Prior Publication Data
US 2021/0212915 A1    Jul. 15, 2021

(30) Foreign Application Priority Data

May 18, 2018  (EP) .................................. 18173222

(51) Int. Cl.
  *A61K 8/49* (2006.01)
  *A61K 8/06* (2006.01)
  *A61K 8/24* (2006.01)
  *A61Q 17/04* (2006.01)
  *A61Q 19/00* (2006.01)

(52) U.S. Cl.
  CPC ............ *A61K 8/4966* (2013.01); *A61K 8/062* (2013.01); *A61K 8/24* (2013.01); *A61Q 17/04* (2013.01); *A61Q 19/00* (2013.01); *A61K 2800/10* (2013.01)

(58) Field of Classification Search
  None
  See application file for complete search history.

(56) References Cited

U.S. PATENT DOCUMENTS

2015/0265510 A1*  9/2015  Johncock .............. C09C 1/3692
                                                            424/59

FOREIGN PATENT DOCUMENTS

| DE | 10 2014 104 257 | 10/2015 |
| EP | 2 921 157 | 9/2015 |
| EP | 3 228 299 | 10/2017 |
| EP | 3 260 113 | 12/2017 |
| EP | 3 269 425 | 1/2018 |
| WO | 01/45640 | 6/2001 |

OTHER PUBLICATIONS

International Search Report for PCT/EP2019/062206 dated Jul. 5, 2019, 4 pages.
Written Opinion of the ISA for PCT/EP2019/062206 dated Jul. 5, 2019, 6 pages.

* cited by examiner

*Primary Examiner* — Dominic Lazaro
(74) *Attorney, Agent, or Firm* — Nixon & Vanderhye P.C.

(57) ABSTRACT

The present invention relates to topical compositions comprising D-panthenol, bis-ethylhexyloxyphenol methoxyphenyl triazine (BEMT) and hydroxyacetophenone (HAP) in specific weight ratios which show less staining.

9 Claims, No Drawings

TOPICAL COMPOSITION

This application is the U.S. national phase of International Application No. PCT/EP2019/062206 filed May 13, 2019 which designated the U.S. and claims priority to EP Patent Application No. 18173222.3 filed May 18, 2018, the entire contents of each of which are hereby incorporated by reference.

The present invention relates to topical compositions comprising D-panthenol, bis-ethylhexyloxyphenol methoxyphenyl triazine (BEMT) and p-hydroxyacetophenone (HAP).

Sun care products have evolved considerably over the years. Earlier formulations were intended to protect the user from UV-B radiation as was once thought that UV-B rays were the most important contributors to wrinkling, skin disease, and skin cancer. However, more recent studies have shown that UV-A radiation is equally or even more important in the development of solar damage and skin diseases, such as lupus erythematosus and melanoma and non-melanoma skin cancer. Thus, today's focus is towards eliminating as much of UVA (320-400 nm) and/or UVB (280-320 nm) light as possible. Consequently, there's a constantly increasing need for sun care products exhibiting high SPF's (Sun Protection Factor) and high UVA protection while being photostable.

In this respect sunscreens generally contain at least one UVA filter such as BEMT, butyl methoxydibenzoylmethane or and diethylamino hydroxybenzoyl hexyl benzoate. UVA filters are however known to stain fabrics. This is a general issue as consumers suffer from yellow stains on their T-shirts after using sunscreens. To prevent this, consumers tend to use less sunscreen but at the same time they are less protected. The adverse effects of UV radiation on skin are well known. It is therefore important for the industry to provide solutions for such kind of issues to guarantee that consumers apply sufficient sunscreen for appropriate protection.

Beside that the consumer is more and more looking for preservative-free formulations or formulations with alternative preservation systems. In this respect hydroxyacetophenone (i.e. p-hydroxyacetophenone, HAP) is used as preservation booster.

It was therefore the object of the present invention to remedy the disadvantages of the prior art and to develop topical compositions, in particular sun care products comprising at least one UVA filter such as in particular BEMT, which exhibit a reduced textile staining respectively facilitate (i.e. improve respectively ease) the removal of such UVA filters out of textiles contaminated therewith.

Surprisingly, it has been found that the addition of D-panthenol in specific amounts to sunscreens comprising BEMT and p-hydroxyacetophenone significantly reduces the textile staining of said compositions and furthermore facilitates the removal thereof by washing.

Thus, the invention relates in one aspect to topical composition comprising BEMT, D-panthenol and p-hydroxyacetophenone, wherein the weight ratio of D-panthenol to BEMT is at least 1, preferably at least 1.1, more preferably at least 1.25, even more preferably at least 1.5, such as most preferably at least 1.75, e.g. at least 2. This means that if the topical composition contains 1 part per weight of BEMT it contains at least 1, preferably at least 1.1, more preferably at least 1.25, such as even more preferably at least 1.5, such as most preferably at least 1.75, e.g. at least 2 parts per weight of D-panthenol.

The term "topical" is understood here to mean external application to keratinous substances, which are in particular the skin, scalp, eyelashes, eyebrows, nails, mucous membranes and hair, preferably the skin.

"BEMT" stands for bis-ethylhexyloxyphenol methoxyphenyl triazine (INCI) or Bemotrizinol (INN) (CAS Number 187393-00-6). BEMT acts as a broad-spectrum UV filter absorbing UVB as well as UVA rays. It has two absorption peaks, 310 and 340 nm. BEMT is suggested for use in sun, day care, alphabetic products such as BB cream, whitening products, color cosmetics.

In all embodiments of the present invention BEMT is advantageously used in an amount selected in the range of 0.4 to 10 wt.-%, preferably in the range of 0.4 to 10 wt.-%, 0.4 to 9 wt.-%, 0.4 to 8 wt.-%, 0.4 to 7 wt.-%, 0.4 to 6 wt.-%, 0.4 to 5 wt.-%, 0.4 to 4 wt.-%, 0.5 to 3 wt.-%, 0.8 to 9 wt.-%, 0.8 to 8 wt.-%, 0.8 to 7 wt.-%, 0.8 to 6 wt.-%, 0.8 to 5 wt.-%, 0.8 to 4 wt.-%, 0.8 to 3 wt.-%, such as for instance in the range from 1 to 5 wt.-%, 2 to 5 wt.-%, or 1 to 3 wt.-%, based on the total weight of the composition.

D-panthenol is also referred to as panthenol (INCI), dexpanthenol, provitamin B5, or (+)-(R)-2,4-dihydroxy-N-(3-hydroxypropyl)-3,3-dimethylbutyramid. D-Panthenol improves hydration, reduces itching and inflammation of the skin, improves skin elasticity, and accelerates epidermal wound healing. The D-panthenol is commercially available and sold for instance by DSM Nutritional Products Europe Ltd.

In all embodiments of the present invention, D-panthenol is advantageously used in an amount selected in the range from 0.45 to 20 wt.-%, preferably in the range from 0.45 to 18 wt.-%, 0.45 to 16 wt.-%, 0.45 to 15 wt.-%, 0.5 to 12.5 wt.-%, 0.5 to 10 wt.-%, 0.5 to 8 wt.-%, more preferably in the range from 0.5 to 6 wt.-%, for instance in the range from 0.5 to 5 wt.-%, based on the total weight of the composition. Even more preferably, the amount of panthenol in the formulations according to the present invention is selected in the range from 0.75 to 5 wt.-%, from 1 to 5 wt.-%, or from 2 to 5 wt.-%.

p-Hydroxyacetophenone, also designated herein as hydroxyacetophenone or HAP (CAS No. 99-93-4) is a multifunctional cosmetic ingredient with anti-oxidant and soothing characteristics. It can be used as a preservation booster which is mild and safe. P-Hydroxyacetophenone is commercially available.

In all embodiments of the present invention p-hydroxyacetophenone is advantageously used in an amount selected in the range from 0.001 to 5 wt.-%, preferably in the range from 0.01 to 4 wt.-%, 0.1 to 3 wt.-%, more preferably in the range from 0.1 to 1.5 wt.-%, based on the total weight of the composition. Further preferred ranges are from 0.005 to 4.5 wt.-%, 0.05 to 3 wt.-%, 0.1 to 2 wt.-%, and 0.25 to 1.5 wt.-%, based on the total weight of the composition.

In a particular advantageous embodiment, the invention relates to topical compositions comprising BEMT, D-panthenol and p-hydroxyacetophenone, wherein the weight ratio D-panthenol to BEMT is selected in the range from 1.1 to 5 (i.e. 1 part per weight of BEMT to 1.1 to 5 parts per weight of D-panthenol), preferably in the range from 1.1 to 4 (i.e. 1 part per weight of BEMT to 1.1 to 4 parts per weight of D-panthenol), most preferably in the range from 1.1 to 3 (i.e. 1 part per weight of BEMT to 1.1 to 3 parts per weight of D-panthenol) such as in particular in the range from 1.15 to 2 (i.e. 1 part per weight of BEMT to 1.15 to 2 parts per weight of D-panthenol).

In all embodiments of the present invention, preferably the topical compositions comprise BEMT, D-panthenol and p-hydroxyacetophenone, wherein the weight ratio (w/w) of HAP to BEMT is selected in the range of 0.01 to 1 (i.e. 1 part per weight of BEMT to 0.01 to 1 part per weight of HAP).

In a further embodiment, the topical composition comprises BEMT, D-panthenol and p-hydroxyacetophenone, wherein the weight ratio of HAP to BEMT is selected in the range of 0.05 to 1 (i.e. 1 part per weight of BEMT to 0.05 to 1 part per weight of HAP), preferably in the range from 0.1 to 1 (i.e. 1 part per weight of BEMT to 0.1 to 1 part per weight of HAP), more preferably 0.2 to 1 (i.e. 1 part per weight of BEMT to 0.2 to 1 part per weight of HAP), most preferably in the range from 0.25 to 1 (i.e. 1 part per weight of BEMT to 0.25 to 1 part per weight of HAP).

In all embodiments of the present invention advantageously the amount of HAP is lower than the amount of BEMT. Thus, in a preferred embodiment, the compositions according to the present invention exhibit a weight ratio of HAP to BEMT of less than 1, such as in the range from 0.05 to 0.9, preferably in the range from 0.1 to 0.75, most preferably in the range from 0.25 to 0.5.

Accordingly, in all embodiments of the present invention, the topical composition preferably comprises BEMT, D-panthenol and p-hydroxyacetophenone, wherein the weight ratio of HAP to BEMT is selected in the range of 1 part per weight of BEMT to 0.05 to 0.9 parts per weight of HAP; 1 part per weight of BEMT to 0.1 to 0.8 parts per weight of HAP, 1 part per weight of BEMT to 0.1 to 0.75 parts per weight of HAP, 1 part per weight of BEMT to 0.2 to 0.6 parts per weight of HAP, or 1 part per weight of BEMT to 0.25 to 0.5 parts per weight of HAP.

In a further embodiment, the topical composition comprises BEMT, D-panthenol and p-hydroxyacetophenone, wherein the weight ratio of D-panthenol to BEMT to is at least 1.1, preferably at least 1.2, and the weight ratio of HAP to BEMT is selected in the range from 0.05 to 0.9.

In a further embodiment, the topical composition comprises BEMT, D-panthenol and p-hydroxyacetophenone, wherein
- the weight ratio of D-panthenol to BEMT is at least 1.15; preferably at least 1.2; for example selected in the range from 1.15 to 5; from 1.15 to 4; from 1.15 to 3; from 1.15 to 2; from 1.15 to 2; and
- the weight ratio of HAP to BEMT is selected in the range of 0.05 to 1; preferably in the range of 0.1 to 1, most preferably in the range of 0.2 to 1, such as in the range of 0.25 to 1; for example in the range of 1 part per weight of BEMT to 0.05-0.9 parts per weight of HAP; 1 part per weight of BEMT to 0.1-0.8 parts per weight of HAP, 1 part per weight of BEMT to 0.1-0.75 parts per weight of HAP, 1 part per weight of BEMT to 0.2-0.6 parts per weight of HAP, 1 part per weight of BEMT to 0.25-0.5 parts per weight of HAP.

Particular preferred topical compositions according to the present invention comprise BEMT, D-panthenol and p-hydroxyacetophenone, wherein the weight ratio of D-panthenol to BEMT is selected in the range from 1.1 to 5, preferably in the range from 1.1 to 4; more preferably in the range from 1.1 to 3; most preferably in the range from 1.1 to 2.5 and the weight ratio of HAP to BEMT is selected in the range from 0.1 to 0.75.

In a further embodiment of the invention, the topical composition comprising BEMT, D-panthenol and p-hydroxyacetophenone is a cosmetic or pharmaceutical composition.

In a further embodiment of the invention, the topical composition comprising BEMT, D-panthenol and p-hydroxyacetophenone is a sun care product (i.e. a sunscreen).

A further embodiment of the invention relates to the use of the topical composition as described above, for reducing the textile (cloth) staining of BEMT, in particular after washing, and/or facilitating the washing of a topical composition according to the present invention out of textiles contaminated therewith. Preferably said composition furthermore comprises p-hydroxyacetophenone.

In another embodiment, the present invention relates to the use of D-panthenol for reducing the textile (cloth) staining caused by UVA filters such as preferably BEMT respectively BEMT in the presence of p-hydroxyacetophenone.

Furthermore, the invention relates to use of D-panthenol in topical compositions containing at least one UVA filter such as preferably BEMT to facilitate the washability of said UVA filter out of textiles contaminated therewith. Said compositions preferably further comprise p-hydroxyacetophenone.

A further embodiment of the invention relates to a method for reducing textile (cloth) staining by topical compositions comprising at least one UVA filter such as preferably BEMT, in particular after washing, said method comprising the incorporation of D-panthenol into said composition. Said compositions preferably further comprise p-hydroxyacetophenone.

In another embodiment, the present invention relates to a method and use to facilitate the washability of topical compositions containing at least one UVA filter such as preferably BEMT out of textiles, said method encompassing the addition of D-panthenol to said composition. Said compositions preferably further comprise p-hydroxyacetophenone.

The term UVA filter as used herein in particular refers to BEMT, butyl methoxydibenzoyl methane [PARSOL® 1789, CAS: 70356-09-1] and diethylamino hydroxybenzoyl hexyl benzoate [UVINUL® A Plus, CAS: 302776-68-7], most preferably to BEMT.

It is well understood, that all preferences and definitions as given herein with regard to the ratios of D-panthenol and BEMT respectively BEMT and p-hydroxyacetophenone also apply to all uses and methods according to the present invention. The same applies for the content (amounts) of BEMT, D-panthenol and p-hydroxyacetophenone. Furthermore, the amounts and ratios given for BEMT also apply to the other UVA filters, i.e. butyl methoxydibenzoyl methane and diethylamino hydroxybenzoyl hexyl benzoate.

In a particular advantageous embodiment, the uses and methods according to the present invention comprise the use of
- a weight ratio of D-panthenol to BEMT of at least 1.15; preferably of at least 1.2; for example selected in the range from 1.15 to 5; from 1.15 to 4; from 1.15 to 3; from 1.15 to 2; from 1.15 to 2; and
- a weight ratio of HAP to BEMT is selected in the range of 0.05 to 1; preferably in the range of 0.1 to 1, most preferably in the range of 0.2 to 1, such as in the range of 0.25 to 1; for example in the range of 1 part per weight of BEMT to 0.05-0.9 parts per weight of HAP; 1 part per weight of BEMT to 0.1-0.8 parts per weight of HAP, 1 part per weight of BEMT to 0.1-0.75 parts per weight of HAP, 1 part per weight of BEMT to 0.2-0.6 parts per weight of HAP, 1 part per weight of BEMT to 0.25-0.5 parts per weight of HAP.

Preferred topical compositions in all embodiments of the present invention are emulsions containing an oily phase and an aqueous phase such as in particular an O/W, W/O, Si/W, W/Si, O/W/O, W/O/W multiple or a pickering emulsions.

The amount of the oily phase (i.e. the phase containing all oils and fats) present in such emulsions is preferably at least 10 wt.-%, such as in the range of 10 to 60 wt.-%, preferably in the range of 15 to 50 wt.-%, most preferably in the range of 15 to 40 wt.-%, based on the total weight of the composition.

According to one preferred embodiment, the topical compositions according to the present invention are O/W emulsions comprising an oily phase dispersed in an aqueous phase in the presence of an O/W emulsifier, preferably in the presence of a cetyl phosphate, such as most preferably potassium cetyl phosphate.

In a further embodiment, the present invention relates to the topical composition according to the embodiments described herein for the use as sunscreen, respectively to the use of the topical composition according to the embodiments described herein as sunscreen.

In a further embodiment, the present invention relates to the use of D-panthenol for facilitating the washing of a composition according to any one of the above described compositions out of textiles contaminated with said composition.

In a further embodiment, the present invention relates to the use of D-panthenol for reducing textile staining caused by bis-ethylhexyloxyphenol methoxyphenyl triazine or bis-ethylhexyloxyphenol methoxyphenyl triazine and p-hydroxyacetophenone.

In a further embodiment, the present invention relates to a method for reducing stains on textiles by a topical composition comprising bis-ethylhexyloxyphenol methoxyphenyl triazine or bis-ethylhexyloxyphenol methoxyphenyl triazine and p-hydroxyacetophenone, said method comprising the incorporation of D-panthenol into said composition.

In a further embodiment, the present invention relates to a method for facilitating the washability of topical compositions containing bis-ethylhexyloxyphenol methoxyphenyl triazine or bis-ethylhexyloxyphenol methoxyphenyl triazine and p-hydroxyacetophenone out of textiles, said method comprising the addition of D-Panthenol to the composition.

Besides the bis-ethylhexyloxyphenol methoxyphenyl triazine (BEMT), further UV filters may be present in the topical composition according to the present invention. These UV filters are all commercially available UV-filter substances such as in particular (INCI names) polysilicone-15, methylene bis-benzotriazolyl tetramethylbutylphenol, tris-biphenyl triazine, phenylbenzimidazol sulfonic acid, 3-benzylidene camphor, octocrylene, ethylhexyl methoxycinnamate, ethylhexyl salicylate, homosalate, ethylhexyl triazone, zinc oxide, diethylhexyl butamido triazone, benzophenon-3, titanium dioxide, butyl methoxydibenzoyl methane, disodium phenyl dibenzimidazole tetrasulfonate and diethylamino hydroxybenzoyl hexyl benzoate without being limited thereto.

Moreover, the topical composition may further comprise a polysilicone-based UV filter. Preferably, the polysilicone-based UV filter has a chromophore residue of the benzalmalonate type. The most preferred polysilicone-based UV is polysilicone-15 (INCI) which is commercially available under the tradename PARSOL® SLX at DSM Nutritional Products Ltd.

The amount of the polysilicone-based UV filter, preferably having a chromophore residue of the benzalmalonate type, such as polysilicone-15, in the compositions according to the present invention is preferably selected in the range 0.1 to 10 wt.-%, such as in the range of 0.5 to 8 wt.-%, such as most preferably in the range of 1 to 5 wt.-% based on the total weight of the composition. Further ranges would be 0.2-10 wt.-%, 0.3-9 wt.-% or 0.4-8 wt.-%.

It is however preferred in all embodiments according to the present invention that the compositions do not contain any polysilicone-15, as this increases the initial staining properties of BEMT (before washing), even though after washing the staining is significantly reduced.

As the topical compositions according to the invention are intended for topical application, they comprise a physiologically acceptable medium, that is to say a medium compatible with keratinous substances, such as the skin, mucous membranes, and keratinous fibers. In particular the physiologically acceptable medium is a cosmetically acceptable carrier.

The term cosmetically acceptable carrier refers to all carriers and/or excipients and/or diluents conventionally used in cosmetic compositions.

Preferred topical compositions according to the invention are skin care preparations, decorative preparations, and functional preparations.

Examples of skin care preparations are, in particular, light protective preparations, anti-ageing preparations, preparations for the treatment of photo-ageing, body oils, body lotions, body gels, treatment creams, skin protection ointments, skin powders, moisturizing gels, moisturizing sprays, face and/or body moisturizers, skin-tanning preparations (i.e. compositions for the artificial/sunless tanning and/or browning of human skin), for example self-tanning creams as well as skin lightening preparations.

Examples of decorative preparations are, in particular, lipsticks, eye shadows, mascaras, dry and moist make-up formulations, rouges and/or powders.

Examples of functional preparations are cosmetic or pharmaceutical compositions containing active ingredients such as hormone preparations, vitamin preparations, vegetable extract preparations, anti-ageing preparations, and/or antimicrobial (antibacterial or antifungal) preparations without being limited thereto.

In a particular embodiment, the topical compositions according to the invention are light-protective preparations (sun care products), such as sun protection milks, sun protection lotions, sun protection creams, sun protection oils, sun blocks or day care creams with a SPF (sun protection factor). Of particular interest are sun protection creams, sun protection lotions, sun protection milks and sun protection preparations.

The topical compositions according to the present invention may be in the form of a suspension or dispersion in solvents or fatty substances, or alternatively in the form of an emulsion or micro emulsion (in particular of oil-in-water (O/W-) or water-in-oil (W/O-)type, silicone-in-water (Si/W-) or water-in-silicone (W/Si-)type, PIT-emulsion, multiple emulsion (e.g. oil-in-water-in oil (O/W/O-) or water-in-oil-in-water (W/O/W-)type), pickering emulsion, hydrogel, alcoholic gel, lipogel, one- or multiphase solution or vesicular dispersion or other usual forms, which can also be applied by pens, as masks or as sprays.

The topical compositions according to the present invention are advantageously in the form of an oil-in-water (O/W) emulsion comprising an oily phase dispersed in an aqueous phase in the presence of an O/W emulsifier. The preparation of such O/W emulsions is well known to a person skilled in the art and illustrated in the examples.

In one advantageous embodiment, the compositions in addition contain a phosphate ester emulsifier. Among the preferred phosphate ester emulsifier are $C_{8-10}$ Alkyl Ethyl Phosphate, $C_{9-15}$ Alkyl Phosphate, Ceteareth-2 Phosphate, Ceteareth-5 Phosphate, Ceteth-8 Phosphate, Ceteth-10 Phosphate, Cetyl Phosphate, C6-10 Pareth-4 Phosphate, $C_{12-15}$ Pareth-2 Phosphate, $C_{12-15}$ Pareth-3 Phosphate, DEA-Ceteareth-2 Phosphate, DEA-Cetyl Phosphate, DEA-Oleth-3 Phosphate, Potassium cetyl phosphate, Deceth-4 Phosphate, Deceth-6 Phosphate and Trilaureth-4 Phosphate. A particular phosphate ester emulsifier according to the invention is potassium cetyl phosphate e.g. commercially available as Amphisol® K at DSM Nutritional Products Ltd Kaiseraugst.

If the topical composition according to the invention is an O/W emulsion, then it preferably contains at least one O/W- or Si/W-emulsifier selected from the list of PEG-30 Dipolyhydroxystearate, PEG-4 Dilaurate, PEG-8 Dioleate, PEG-40 Sorbitan Peroleate, PEG-7 Glyceryl Cocoate, PEG-20 Almond Glycerides, PEG-25 Hydrogenated Castor Oil, Glyceryl Stearate (and) PEG-100 Stearate, PEG-7 Olivate, PEG-8 Oleate, PEG-8 Laurate, PEG-60 Almond Glycerides, PEG-20 Methyl Glucose Sesquistearate, PEG-40 Stearate, PEG-100 Stearate, PEG-80 Sorbitan Laurate, Steareth-2, Steareth-12, Oleth-2, Ceteth-2, Laureth-4, Oleth-10, Oleth-10/Polyoxyl 10 Oleyl Ether, Ceteth-10, Isosteareth-20, Ceteareth-20, Oleth-20, Steareth-20, Steareth-21, Ceteth-20, Isoceteth-20, Laureth-23, Steareth-100, glycerylstearatcitrate, glycerylstearate (self-emulsifying), stearic acid, salts of stearic acid, polyglyceryl-3-methylglycosedistearate. Further suitable emulsifiers are sorbitan oleate, sorbitan sesquioleate, sorbitan isostearate, sorbitan trioleate, Lauryl Glucoside, Decyl Glucoside, Sodium Stearoyl Glutamate, Sucrose Polystearate and Hydrated Polyisobuten. Furthermore, one or more synthetic polymers may be used as an emulsifier. For example, PVP eicosene copolymer, acrylates/ $C_{10-30}$ alkyl acrylate crosspolymer, acrylates/steareth-20 methacrylate copolymer, PEG-22/dodecyl glycol copolymer, PEG-45/dodecyl glycol copolymer, and mixtures thereof.

Another particular suitable class of O/W emulsifiers are non-ionic self-emulsifying system derived from olive oil e.g. known as (INCI Name) cetearyl olivate and sorbitan olivate (Chemical Composition: sorbitan ester and cetearyl ester of olive oil fatty acids) sold under the tradename OLIVEM 1000.

Further suitable are commercially available polymeric emulsifiers such as hydrophobically modified polyacrylic acid such as Acrylates/C10-30 Alkyl Acrylate Crosspolymers which are commercially available under the tradename Pemulen® TR-1 and TR-2 by Noveon.

Another class of particularly suitable emulsifiers are polyglycerol esters or diesters of fatty acids also called polyglyceryl ester/diester (i.e. a polymer in which fatty acid(s) is/are bound by esterification with polyglycerine), such as e.g. commercially available at Evonik as Isolan GPS [INCI Name Polyglyceryl-4 Diisostearate/Polyhydroxystearate/Sebacate (i.e. diester of a mixture of isostearic, polyhydroxystearic and sebacic acids with Polyglycerin-4)] or Dehymuls PGPH available at Cognis (INCI Polyglyceryl-2 Dipolyhydroxystearate).

Also suitable are polyalkylenglycolether such as Brij 72 (Polyoxyethylen(2)stearylether) or Brij 721 (Polyoxyethylene (21) Stearyl Ether e.g. available at Croda.

The at least one O/W respectively Si/W emulsifier is preferably used in an amount of 0.5 to 10 wt.-% such as in particular in the range of 0.5 to 5 wt.-% such as most in particular in the range of 0.5 to 4 wt.-% based on the total weight of the composition.

Suitable W/O- or W/Si-emulsifiers are polyglyceryl-2-dipolyhydroxystearat, PEG-30 dipolyhydroxystearat, cetyl dimethicone copolyol, polyglyceryl-3 diisostearate polyglycerol esters of oleic/isostearic acid, polyglyceryl-6 hexaricinolate, polyglyceryl-4-oleate, polygylceryl-4 oleate/PEG-8 propylene glycol cocoate, magnesium stearate, sodium stearate, potassium laurate, potassium ricinoleate, sodium cocoate, sodium tallowate, potassium castorate, sodium oleate, and mixtures thereof. Further suitable W/Si-emulsifiers are Lauryl Polyglyceryl-3 Polydimethylsiloxyethyl Dimethicone and/or PEG-9 Polydimethylsiloxyethyl Dimethicone and/or Cetyl PEG/PPG-10/1 Dimethicone and/ or PEG-12 Dimethicone Crosspolymer and/or PEG/PPG-18/18 Dimethicone. The at least one W/O emulsifier is preferably used in an amount of about 0.001 to 10 wt.-%, more preferably in an amount of 0.2 to 7 wt.-% with respect to the total weigh of the composition.

The topical compositions according to the present invention furthermore advantageously contain at least one co-surfactant such as e.g. selected from the group of mono- and diglycerides and/or fatty alcohols. The co-surfactant is generally used in an amount selected in the range of 0.1 to 10 wt.-%, such as in particular in the range of 0.5 to 6 wt.-%, such as most in particular in the range of 1 to 5 wt.-%, based on the total weight of the composition. Particular suitable co-surfactants are selected from the list of alkyl alcohols such as cetyl alcohol (Lorol C16, Lanette 16), cetearyl alcohol (Lanette O), stearyl alcohol (Lanette 18), behenyl alcohol (Lanette 22), glyceryl stearate, glyceryl myristate (Estol 3650), hydrogenated coco-glycerides (Lipocire Na10) as well as mixtures thereof The compositions in form of O/W emulsions according to the invention can be provided, for example, in all the formulation forms for O/W emulsions, for example in the form of serum, milk or cream, and they are prepared according to the usual methods. The compositions which are subject-matters of the invention are intended for topical application and can in particular constitute a dermatological or cosmetic composition, for example intended for protecting human skin against the adverse effects of UV radiation (antiwrinkle, anti-ageing, moisturizing, anti-sun protection and the like).

According to an advantageous embodiment of the invention the compositions constitute cosmetic composition and are intended for topical application to the skin.

Finally, a subject-matter of the invention is a method for the cosmetic treatment of keratinous substances such as in particular the skin, wherein a composition as defined above is applied to the said keratinous substances such as in particular to the skin. The method is in particular suitable to protect the skin against the adverse effects of UV-radiation such as in particular sun-burn and/or photoageing.

In accordance with the present invention, the compositions according to the invention may comprise further ingredients such as ingredients for skin lightening; tanning prevention; treatment of hyperpigmentation; preventing or reducing acne, wrinkles, lines, atrophy and/or inflammation; chelators and/or sequestrants; anti-cellulites and slimming (e.g. phytanic acid), firming, moisturizing and energizing, self-tanning, soothing, as well as agents to improve elasticity and skin barrier and/or further UV-filter substances, blue light protection agents and carriers and/or excipients or diluents conventionally used in topical compositions. If nothing else is stated, the excipients, additives, diluents, etc. mentioned in the following are suitable for topical compositions according to the present invention. The necessary amounts of the cosmetic and dermatological adjuvants and additives can, based on the desired product, easily be determined by the skilled person. The additional ingredients can either be added to the oily phase, the aqueous phase or separately as deemed appropriate. The mode of addition can easily be adapted by a person skilled in the art.

The cosmetically active ingredients useful herein can in some instances provide more than one benefit or operate via more than one mode of action.

The topical cosmetic compositions of the invention can also contain usual cosmetic adjuvants and additives, such as preservatives/antioxidants, fatty substances/oils, water, organic solvents, silicones, thickeners, softeners, emulsifiers, sunscreens, antifoaming agents, moisturizers, aesthetic components such as fragrances, surfactants, fillers, sequestering agents, anionic, cationic, nonionic or amphoteric polymers or mixtures thereof, propellants, acidifying or basifying agents, dyes, colorings/colorants, abrasives, absorbents, essential oils, skin sensates, astringents, antifoaming agents, pigments or nanopigments, e.g. those suited for providing a photoprotective effect by physically blocking out ultraviolet radiation, or any other ingredients usually formulated into cosmetic compositions. Such cosmetic ingredients commonly used in the skin care industry, which are suitable for use in the compositions of the present invention are for example described in the International Cosmetic Ingredient Dictionary & Handbook by Personal Care Product Council (http://www.personal carecouncil.org/), accessible by the online INFO BASE (http://online.personalcarecouncil.org/jsp/Home.jsp), without being limited thereto.

The necessary amounts of the cosmetic and dermatological adjuvants and additives can—based on the desired product—easily be chosen by a skilled person in this field and will be illustrated in the examples, without being limited hereto.

Of course, one skilled in this art will take care to select the above mentioned optional additional compound or compounds and/or their amounts such that the advantageous properties intrinsically associated with the combination in accordance with the invention are not, or not substantially, detrimentally affected by the envisaged addition or additions.

The topical compositions according to the invention in general have a pH in the range of 3 to 10, preferably a pH in the range of 4 to 8 and most preferably a pH in the range of 4 to 7. The pH can easily be adjusted as desired with suitable acids such as e.g. citric acid or bases such as NaOH according to standard methods in the art.

The topical compositions according to the invention may further contain one or more emollients which soothe and soften the skin. As an example, the emollient may be dicaprylyl carbonate or $C_{12-15}$alkyl benzoate. Further emollients are silicone (dimethicone, cyclomethicone), vegetable oils (grape seed, sesame seed, jojoba, etc.), butters (cocoa butter, shea butter), alcohols (stearyl alcohol, cetyl alcohol), and petrolatum derivatives (petroleum jelly, mineral oil).

The cosmetic compositions according to the present invention advantageously comprise preservatives or preservative booster. Preferably, the additional preservatives respectively preservative boosters are selected from the group consisting of phenoxyethanol, ethylhexylglycerin, glyceryl caprylate, caprylyl glycol, 1,2-hexanediol, propanediol, propylene glycol, as well as mixtures thereof. When present, the preservative respectively preservative booster is preferably used in an amount of 0.01 to 2 wt.-%, more preferably in an amount of 0.05 to 1.5 wt.-%, most preferably in an amount of 0.1 to 1.0 wt.-%, based on the total weight of the composition. It is particularly preferred, that the cosmetic compositions according to the invention does not contain any further/other preservatives such as e.g. parabens and/or methylisothiazolinone.

The following examples are provided to further illustrate the compositions and effects of the present invention. These examples are illustrative only and are not intended to limit the scope of the invention in any way.

EXPERIMENTAL PART

Cream formulations as outlined in table 1 have been prepared. Afterwards, cream has been applied on a cotton fabric with the following procedure: The textile (A5 size cut piece of a cotton textile) is fixed on top of a plastic bottle with an elastic strap. Bottle with fixed textile is placed on a balance. 0.36 g (+/−0.1 g) of sunscreen formulation is weighed on the fabric and homogenously distributed on an area with 5 cm diameter. Then the fabric has been dried for 15 minutes followed by measuring the L,a,b value of the spot.

Afterwards, the fabric has been washed for 1 h in a beaker with 300 ml water and 1 g detergent at 40° C. under stirring, followed by rinsing the fabric in 300 ml fresh water for 15 minutes. After the fabric has been dried for 15 minutes the L,a,b value of the spot has been measured again. For each trial 3 separate fabrics have been used and accordingly each result is the average of 3 fabrics.

Explanation of b value: the higher the b value, the more yellow is the fabric; the more negative the number is, the more white/bluish is the fabric.

TABLE 1

| Ingredient | Reference 1 | Reference 2 | Invention 1 | Invention 2 |
|---|---|---|---|---|
| | Wt.-% | | | |
| Potassium Cetyl Phosphate | 1.5 | 1.5 | 1.5 | 1.5 |
| Stearyl Alcohol | 3.0 | 3.0 | 3.0 | 3.0 |
| Tridecyl Salicylate | 11.0 | 11.0 | 11.0 | 11.0 |
| C12-15 Alkyl Benzoate | 11.0 | 11.0 | 11.0 | 11.0 |
| Bis-Ethylhexyloxyphenol Methoxyphenyl Triazine (BEMT) | 2.5 | 2.5 | 2.5 | 2.5 |
| Hydroxyacetophenone (HAP) | 0.7 | 0.7 | 0.7 | 0.7 |
| Aqua | q.s. | q.s. | q.s. | q.s. |
| Glycerin | 3.0 | 3.0 | 3.0 | 3.0 |
| Xanthan Gum | 0.3 | 0.3 | 0.3 | 0.3 |
| Phenoxyethanol, Ethylhexylglycerin | 0.5 | 0.5 | 0.5 | 0.5 |
| D-Panthenol | / | 1.0 | 3.0 | 5.0 |

TABLE 2

| | Reference 1 | Reference 2 | Invention 1 | Invention 2 |
|---|---|---|---|---|
| b value before washing | 4.48 | 4.50 | 4.32 | 3.97 |
| Reduction of yellow staining after washing vs. reference 1 | | No reduction | −4% | −11% |
| b value after washing | −1.05 | −1.02 | −1.42 | −2.07 |
| Reduction of yellow staining after washing vs. reference 1 | | No reduction | −35% | −97% |

As can be retrieved from table 2, the addition of high amounts of D-panthenol to a topical composition comprising BEMT significantly reduced the staining thereof.

The invention claimed is:

1. A topical composition exhibiting reduced textile staining, the topical composition comprising:
   (i) bis-ethylhexyloxyphenol methoxyphenyl triazine,
   (ii) 3.0 to 20.0 wt. %, based on total weight of the composition, of D-panthenol, and
   (iii) p-hydroxyacetophenone,
   wherein a weight-ratio of the D-panthenol to the bis-ethylhexyloxyphenol methoxyphenyl triazine is at least 1.1,
   wherein a weight ratio of the p-hydroxyacetophenone to the bis-ethylhexyloxyphenol methoxyphenyl triazine is in a range of 0.05 to 1, and
   wherein the topical composition exhibits a reduction of yellow staining of a textile after washing by 35% or more as compared to a topical composition not having the weight ratio of the D-panthenol to the bis-ethylhexyloxyphenol methoxyphenyl triazine of at least 1.1.

2. The topical composition according to claim 1, wherein the ratio of the D-panthenol to the bis-ethylhexyloxyphenol methoxyphenyl triazine is at least 1.5.

3. The topical composition according to claim 1, wherein the weight ratio of the D-panthenol to the bis-ethylhexyloxyphenol methoxyphenyl triazine is at least 1.75.

4. The topical composition according to claim 1, wherein the D-panthenol is present in an amount of 3.0 to 5 wt. %.

5. The topical composition according to claim 1, wherein the bis-ethylhexyloxyphenol methoxyphenyl triazine is present in an amount from 0.4 to 10 wt. %, based on the total weight of the composition.

6. The topical composition according to claim 1, wherein the p-hydroxyacetophenone is present in an amount of 0.001 to 5 wt. %, based on the total weight of the composition.

7. The topical composition according to claim 1, wherein the composition is a cosmetic or pharmaceutical composition.

8. The topical composition according to claim 1, wherein the composition is a sun care product.

9. The topical composition according to claim 1, wherein the composition is an oil-in-water (O/W) emulsion comprising an oily phase dispersed in an aqueous phase in the presence of potassium cetyl phosphate as an O/W emulsifier.

* * * * *